United States Patent
Furukawa et al.

(10) Patent No.: US 7,078,562 B2
(45) Date of Patent: Jul. 18, 2006

(54) ADAMANTANE DERIVATIVES AND RESIN COMPOSITIONS USING THE SAME AS RAW MATERIAL

(75) Inventors: Kikuo Furukawa, Ibaraki (JP); Minoru Kakuda, Chiba (JP); Yoshio Nishimura, Ibaraki (JP); Toshiaki Yamada, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/032,095

(22) Filed: Jan. 11, 2005

(65) Prior Publication Data

US 2005/0158662 A1 Jul. 21, 2005

(30) Foreign Application Priority Data

Jan. 19, 2004 (JP) .............................. 2004-010846
Jun. 1, 2004 (JP) .............................. 2004-162663

(51) Int. Cl.
*C07C 69/62* (2006.01)
(52) U.S. Cl. ...................... 560/219; 560/220; 560/223
(58) Field of Classification Search .............. 560/205, 560/219, 220, 223, 226; 568/816, 818, 819, 568/820, 822
See application file for complete search history.

(56) References Cited

U.S. PATENT DOCUMENTS 6,344,590 B1 * 2/2002 Nakano et al. ............. 568/591

FOREIGN PATENT DOCUMENTS

JP 2004069921 * 3/2004

OTHER PUBLICATIONS

Heagy et al., Journal of Organic Chemistry (1995), 60(22), 7351-4.*

* cited by examiner

Primary Examiner—Johann Richter
Assistant Examiner—Karl Puttlitz
(74) Attorney, Agent, or Firm—Antonelli, Terry, Stout and Kraus, LLP.

(57) ABSTRACT

The adamantane derivatives of the present invention which are represented by the general formula (1):

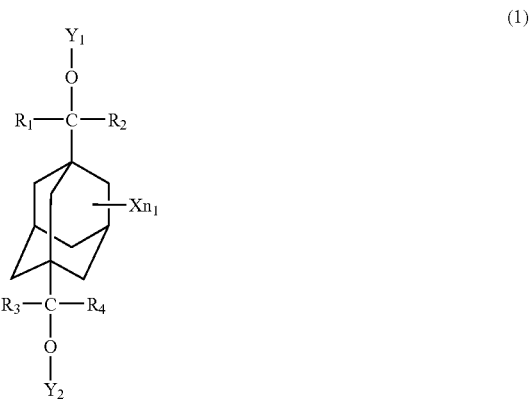

(1)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and $Y_1$ and $Y_2$ may be the same or different from each other and are independently a hydrogen atom or a group represented by the general formula (2):

(2)

wherein $R_5$ to $R_7$ may be the same or different from each other and are independently a hydrogen atom, alkyl, halogen or halogen-containing alkyl, are excellent in optical properties, heat resistance and acid-dissociating property, and useful as crosslinking-type resins, optical materials such as optical fibers, light wave guides, optical disk substrates and photoresists as well as raw materials thereof, intermediate products of medicines or agricultural chemicals, and various other industrial products.

4 Claims, 4 Drawing Sheets

ADAMANTANE DERIVATIVES AND RESIN COMPOSITIONS USING THE SAME AS RAW MATERIAL

BACKGROUND OF THE INVENTION

1. Field of the Invention

The present invention relates to novel adamantane derivatives having an adamantane skeleton which are excellent in optical properties, heat resistance, acid-dissociating property, etc., and useful as crosslinking-type resins, optical materials such as optical fibers, light wave guides and photoresists and raw materials thereof, intermediate products of medicines and agricultural chemicals, or various other industrial products.

In addition, the invention relates to functional resin compositions that are usable as raw resist materials for KrF, ArF or $F_2$ excimer laser, or chemically-amplified type resists for X-rays, electron beams or EUV (extreme ultraviolet rays), as well as acrylate compounds having an adamantane skeleton which are used as raw materials of the compositions.

2. Description of the Related Arts

It is known that since adamantane has a rigid structure and a high symmetry, and derivatives thereof exhibit specific functions, these compounds are useful as high-functional resin materials, intermediate products of medicines, and optical materials (refer to Japanese Patent Publication No. Hei 1(1989)-53633 and Japanese Patent Application Laid-open No. Hei 6(1994)-305044) as well as photoresists (refer to Japanese Patent Application Laid-open No. Hei 4(1992)-39665).

On the other hand, the functional resin compositions used as a resist in semiconductor production processes are required to have well-balanced properties including an ability of rendering light-irradiated portions thereof alkali-soluble, etching resistance, adhesion to substrate and transparency to light irradiated from a light source. As the resist suitable for KrF excimer laser or a light source with a shorter emission wavelength than that of the KrF excimer laser, there are generally known chemically-amplified type resists. The chemically-amplified type resists are usually used in the form of a solution containing the functional resin composition as a main component as well as a photo-acid generator and several kinds of other additives. It is important that among these components, the functional resin composition as a main component exhibits the above respective properties in a well-balanced manner since a performance of the resist is determined by these properties.

In the chemically-amplified type resists for KrF excimer laser or a light source with a shorter emission wavelength than that of the KrF excimer laser, the functional resin composition as a main component thereof generally comprises a polymer containing repeating units such as acrylates. However, the polymer is not composed of a single kind of repeating unit. The reason therefor is that the composition containing a polymer composed of a single kind of repeating unit is incapable of satisfying all of the above properties such as etching resistance. In fact, plural kinds, i.e., two or more kinds of repeating units having functional groups for improving the respective properties are used in the form of a copolymer in the functional resin composition. As resins contained in the resist composition, there have been proposed hydroxystyrene-based resins for resists used in KrF excimer laser lithography, and acrylic resins containing 2-alkyl-2-adamantyl methacrylate as a basic skeleton for resists used in ArF excimer laser lithography (refer to Japanese Patent Application Laid-open Nos. Hei 4(1992)-39665 and Hei 10(1998)-319595).

In recent years, fine processing techniques in lithographic processes have rapidly proceeded. In particular, light sources used in the processes are required to enable formation of images with a line width as narrow as about one-third of a wavelength of light emitted therefrom. With narrowness of the line width, it has been more strictly required to improve resolution and ling edge roughness. One of the reasons therefor is non-uniformity of the functional resin composition due to large difference between properties of the respective repeating units contained therein (refer to "SEMICON JAPAN SEMI Technology Symposium 2002", 3-27). Further, there have been proposed resist compositions containing an adamantanecarboxylic acid derivative which are alkali-soluble and have a good etching resistance (refer to Japanese Patent Application Laid-open No. 2000-122295). Also, there have been proposed resist compositions having a low surface roughness and a low line edge roughness upon etching which comprise a copolymer whose main chain is composed of an acrylic ester derivative, as a single kind of repeating unit, containing as its basic skeleton an acrylate such as typically 2-(1-adamantyl)-2-methacryloyloxypropane (refer to Japanese Patent Application Laid-open No. 2003-167346).

However, in many cases, the repeating units contained in these compositions satisfy only one or two of the properties required for the chemically-amplified type resists such as etching resistance, alkali developability and adhesion to substrate. Therefore, in order to meet the above strict requirements, 3 or 4 kinds of repeating units must be contained in the compositions, and the number of the repeating units to be contained in the compositions tends to increase more and more. For this reason, it becomes more difficult to allow the compositions to have a good uniformity and therefore sufficiently meet the requirements concerning resolution and line edge roughness thereof.

Under these circumstances, it has been strongly demanded to develop functional resin compositions that are free from adverse influences on basic properties thereof, and excellent in alkali developability and adhesion to substrate so as to improve resolution and line edge roughness thereof.

SUMMARY OF THE INVENTION

An object of the present invention is to provide adamantane derivatives having an adamantane skeleton which are useful as crosslinking-type resins having excellent optical properties, and monomers used for production thereof.

Another object of the present invention is to provide functional resin compositions that are used as chemically-amplified type resists sensitive to KrF excimer laser, ArF excimer laser, $F_2$ excimer laser or far ultraviolet rays such as typically EUV, and excellent in alkali developability and adhesion to substrate so as to achieve improvement in resolution and line edge roughness thereof without any significant damage to basic properties required for the resists such as pattern formability, dry-etching resistance and heat resistance, as well as raw compounds thereof.

As the result of extensive researches for solving the above problems, the present inventors have found that the adamantane derivatives represented by the general formula (1):

(1)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and $Y_1$ and $Y_2$ may be the same or different from each other and are independently a hydrogen atom or a group represented by the general formula (2):

(2)

wherein $R_5$ to $R_7$ may be the same or different from each other and are independently a hydrogen atom, alkyl, halogen or halogen-containing alkyl, are suitable for achieving above objects, and can be efficiently produced by specific processes.

Further, the inventors have found that the functional resin compositions containing repeating units represented by the general formula (3):

(3)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and $Y_3$ and $Y_4$ may be the same or different from each other and are independently a hydrogen atom or a group represented by the general formula (4):

(4)

wherein $R_5$ to $R_7$ may be the same or different from each other and are independently a hydrogen atom, alkyl, halogen or halogen-containing alkyl, are useful as photoresists.

The present invention has been accomplished on the basis of the above findings.

The functional resin composition of the present invention has an excellent etching resistance, is capable of forming fine patterns with a high accuracy, and further exhibits an excellent adhesion to substrate as well as a good alkali solubility. Thus, fine patterns with a high accuracy can be formed using the functional resin composition of the present invention.

DETAILED DESCRIPTION OF THE INVENTION

First, the adamantane derivative and the functional resin composition containing the same as a raw material according to the present invention are explained. The compound represented by the general formula (1) can be produced by introducing carboxyl groups into an adamantane ring of adamantanes represented by the general formula (5):

(5)

wherein $Y_5$ and $Y_6$ may be the same or different from each other and are independently a hydrogen atom, hydroxyl or halogen; X is a hydrogen atom, alkyl, halogen-containing alkyl, halogen, or hydroxyl-, halogen-, nitrile- or ether-containing hydrocarbyl, and a plurality of X groups, if any, may be the same or different from each other; and $n_1$ is an integer of 1 to 14, to obtain 1,3-adamantanedicarboxylic acids or derivatives thereof represented by the general formula (6):

(6)

wherein X is the same as defined in general formula (1); and $n_1$ is an integer of 1 to 14.

Examples of the adamantanes represented by the general formula (5) include adamantane and 1,3-substituted adamantanes. Specific examples of the 1,3-substituted adamantanes include 1,3-adamantane diol, 1,3-dibromoadamantane, 1-bromo-3-hydroxyadamantane, 1,3-dichloroadamantane, 1-chloro-3-hydroxyadamantane, 1-hydroxy-3-adamantanecarboxylic acid, 1-bromo-3-adamantanecarboxylic acid and 1-chloro-3-adamantanecarboxylic acid. Of these 1,3-substituted adamantanes, the use of 1,3-adamantane diol is especially preferred since the 1,3-adamantanedicarboxylic acids represented by the general formula (6) can be produced therefrom with a high selectivity and a high yield.

The carboxyl groups may be introduced in the above adamantanes by the method of reacting the adamantanes with carbon monoxide and oxygen in the presence of a protonic acid. When the above reaction is conducted in the presence of the protonic acid, the reaction can smoothly proceed, and the aimed compound can be produced with a high selectivity and a high yield. The protonic acid may be used as a solvent. Examples of the protonic acid include organic acids, e.g., organic carboxylic acids such as formic acid, acetic acid, propionic acid, oxalic acid, citric acid and tartaric acid, and organic sulfonic acids such as methanesulfonic acid, benzenesulfonic acid and p-toluenesulfonic acid, as well as inorganic acids such as hydrochloric acid, sulfuric acid, nitric acid and phosphoric acid.

Also, formic acid, etc., may be used as a carbon monoxide source instead of carbon monoxide itself. For example, it is known that formic acid is decomposed in concentrated sulfuric acid to generate carbon monoxide. In addition, in the case where such a raw material already containing required oxygen atom such as 1,3-adamantane diol is used instead of oxygen, or an oxidizing acid such as sulfuric acid and nitric acid is used as the protonic acid, the use of oxygen is unnecessary.

The carboxyl groups may be introduced into the adamantanes in an inert organic solvent. Examples of the organic solvent include organic carboxylic acids such as acetic acid; nitriles such as acetonitrile and benzonitrile; amides such as formamide, acetamide, dimethylformamide and dimethylacetamide; alcohols such as t-butanol and t-amyl alcohol; aliphatic hydrocarbons such as hexane and octane; aromatic hydrocarbons such as benzene; halogenated hydrocarbons; nitro compounds; esters such as ethyl acetate; ethers such as diethyl ether, diisopropyl ether and dioxane; and mixed solvents thereof. The above carboxylation reaction may smoothly proceed even under a relatively moderate condition. The reaction temperature is, for example, in the range of −78 to 200° C. and preferably about 0 to 100° C. In many cases, the reaction may be usually conducted at a temperature of 10 to 80° C. In addition, the reaction may also be conducted under ordinary pressure or under applied pressure.

The carbon monoxide and oxygen used in the carboxylation reaction may be pure ones or may be diluted with an inert gas. Further, air or ozone may be used as an oxygen source. The amount of carbon monoxide used may be selected from the range of 1 to 1000 equivalents, preferably 1.5 to 100 equivalents and more preferably about 2 to 10 equivalents based on one equivalent of the base material (in this case, if two carboxyl groups are to be introduced, carbon monoxide is used in an amount of 2 moles based on one mole of the base material). The amount of formic acid used instead of carbon monoxide may be determined such that the equivalent amount of carbon monoxide generated therefrom lies in the same range as described above. The amount of oxygen used may be selected from the range of 0 to 1000 equivalents, preferably 0 to 100 equivalents and more preferably 0 to 12 equivalents based on one equivalent of the base material.

Of these methods, preferred is the method of using 1,3-adamantane diol derivatives as the raw adamantane compounds, concentrated sulfuric acid as the protonic acid, and formic acid as the carbon monoxide source, since such a method can be conducted by a simple and moderate liquid phase reaction, and enables the aimed 1,3-adamantanecarboxylic acid derivatives to be produced with a high selectivity and a high yield.

The 1,3-adamantanedicarboxylic acids obtained by the above method are reacted directly or after introducing protective groups thereinto as represented by the general formula (7):

(7)

wherein $Y_7$ and $Y_8$ may be the same or different from each other and are independently a hydrogen atom or hydrocarbyl; X is a hydrogen atom, alkyl, halogen-containing alkyl, halogen, or hydroxyl-, halogen-, nitrile- or ether-containing hydrocarbyl, and a plurality of X groups, if any, may be the same or different from each other; and $n_1$ is an integer of 1 to 14, with a corresponding organic metal compound such as alkyl lithium and Grignard reagent or the organic compound/metal which are represented by the general formulae (8) to (11):

$$R_8MgZ \quad (8);$$

$$R_8Li \quad (9);$$

$$R_8Z \text{ and } Mg \quad (10); \text{ and}$$

$$R_8Z \text{ and } Li \quad (11),$$

wherein $R_8$ is a hydrocarbon group or halogen-containing alkyl; and Z is halogen, to obtain a 1,3-adamantanedialkyl alcohol compound (hereinafter referred to merely as "adamantane dialcohol compound") represented by the general formula (12):

(12)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; and $R_1$ to $R_4$ may be the same or different from each other and are independently alkyl or halogen-containing alkyl.

As the organic metal compound, there may be used known organic metal compounds such as alkyl lithium and Grignard reagents. Further, the above reaction may be conducted in the form of a Barbier reaction using by one pot a halogenated compound/metal such as lithium and magnesium from which the organic metal compound can be derived (all of the compounds or combinations represented by the general formulae (8) to (11) are hereinafter referred to merely as "organic metal compound"). For example, upon production of 1,3-di(2-hydroxy-2-propyl)adamantane, the corresponding organic metal compound such as methyl lithium and methyl bromide magnesium acts as a methyl-introducing reagent. The reaction of the adamantane compound with the alkyl lithium and Grignard reagent may be conducted according to ordinary Grignard reaction procedure. The amount of the alkyl lithium or Grignard reagent used is in the range of 1 to 10 equivalents and preferably 1 to 2 equivalents based on one equivalent of the above adamantane compound, in which one equivalent of the alkyl lithium or Grignard reagent used means the number of moles of alkyl groups required for reacting with one mole of the raw compound. In addition, the amount of the organic metal compound used increases according to the number of carboxyl groups or hydroxyl groups to be introduced into the raw compound. The reaction may be conducted in ethers such as diethyl ether and tetrahydrofuran, etc. The reaction temperature is, for example, in the range of –20 to 150° C. and preferably about 0 to 100° C.

The protective groups for the carboxyl groups may be introduced by ordinary methods. Examples of the protective groups for the carboxyl groups include alkoxy groups such as methoxy, ethoxy and t-butoxy; aralkyloxy groups such as benzyloxy, p-methoxybenzyloxy, diphenylmethyloxy and benzhydryloxy; and N-hydroxysuccinimide.

The thus produced adamantanedialcohol compound is esterified with (meth)acrylic acid or a derivative thereof (hereinafter referred to merely as "acrylic compound") to obtain the aimed compound represented by the general formula (1). The adamantanedialcohol compound may be used directly or in the form of a compound obtained by substituting hydroxyl groups of the adamantanedialcohol compound with alkali metal such as lithium and sodium or halogenated magnesium, which is represented by the general formula (13):

(13)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and $Y_9$ and $Y_{10}$ may be the same or different from each other and are independently a hydrogen atom, an alkali metal such as potassium, sodium and lithium, or halogenated magnesium.

The reaction of the adamantanedialcohol compound with the acrylic compound represented by the general formula (14) or (15):

(14)

wherein $R_5$ to $R_7$ may be the same or different from each other and are independently a hydrogen atom, alkyl, halogen or halogen-containing alkyl; and $Y_{11}$ is hydroxyl, alkoxy or halogen; or (15)

wherein $R_5$ to $R_7$ may be the same or different from each other and are independently a hydrogen atom, alkyl, halogen or halogen-containing alkyl, may be conducted by ordinary methods using acid catalysts, base catalysts or transesterification catalysts Specific examples of the acrylic compounds include acid compounds such as acrylic acid, methacrylic acid, 2-fluoroacrylic acid, trifluoroacrylic acid and 2-(trifluoromethyl)

acrylic acid; acrylic halides such as acrylic chloride, methacrylic chloride, 2-fluoroacrylic chloride, trifluoroacrylic chloride and 2-(trifluoromethyl)acrylic chloride; acrylic esters such as methyl acrylate, ethyl acrylate, t-butyl acrylate, methyl methacrylate, ethyl methacrylate, t-butyl methacrylate, methyl trifluoroacrylate, ethyl trifluoroacrylate, isopropyl trifluoroacrylate, t-butyl trifluoroacrylate, methyl pentafluoromethacrylate, ethyl pentafluoromethacrylate, isopropyl pentafluoromethacrylate, t-butyl pentafluoromethacrylate, methyl 2-fluoroacrylate, ethyl 2-fluoroacrylate, isopropyl 2-fluoroacrylate, t-butyl 2-fluoroacrylate, methyl 2-(trifluoromethyl)acrylate, ethyl 2-(trifluoromethyl)acrylate, isopropyl 2-(trifluoromethyl)acrylate and t-butyl 2-(trifluoromethyl)acrylate; acrylic acid salts such as sodium acrylate, sodium methacrylate, sodium 2-fluoroacrylate, sodium trifluoroacrylate and sodium 2-(trifluoromethyl)acrylate; and acrylic anhydrides such as acrylic anhydride, methacrylic anhydride, pentafluoroacrylic anhydride, pentafluoromethacrylic anhydride, 2,2'-difluoroacrylic anhydride, 2-fluoroacrylic anhydride and 2-trifluoromethylacrylic anhydride. The amount of the acrylic compound used is in the range of 1 to 100 equivalents and preferably 1 to 10 equivalents (in terms of acryloyloxy groups required) based on one equivalent of the raw compound. If the amount of the acrylic compound used is less than the above-specified range, the yield of the aimed compound tends to be lowered. On the other hand, if the amount of the acrylic compound used exceeds the above-specified range, such a process tends to be uneconomical.

In order to rapidly react the adamantanedialcohol compound with the acrylic compound at a high yield, the reaction therebetween is preferably conducted in the presence of additives. In particular, when acid halides or acrylic anhydrides are used as the acrylic compound, it is desirable that the reaction is conducted in the presence of basic compounds as the additives. More specifically, when an acid halide compound or an acrylic anhydride such as typically acrylic chloride, methacrylic chloride, acrylic anhydride and methacrylic anhydride is used as the acrylic compound, the existence of the basic compounds in the reaction system allows the reaction to rapidly proceed, thereby producing the aimed compound at a high yield. In this case, even though the basic compounds tend to be readily eliminated by the action of acid catalysts, it is possible to obtain the aimed compound at a sufficiently high yield. The basic compounds added are preferably organic bases such as amine compounds. Examples of the amine compounds include amines such as methylamine, dimethylamine, trimethylamine, ethylamine, diethylamine, triethylamine, n-propylamine, di-n-propylamine, diisopropylamine, tri-n-propylamine, n-butylamine, di-n-butylamine, diisopropylamine, tri-n-butylamine, diphenyl amine, 1,5-diazabicyclo[4.3.0]nonene-5, 1,5-diazabicyclo[5.4.0]undecene-5 and diazabicyclo[2.2.2]octane. Of these amine compounds, triethylamine is especially preferred in view of its high effect. Further, the reaction solution may also contain nitrogen-containing heterocyclic compounds, e.g., anilines such as aniline, methyl aniline, dimethyl aniline, toluidine, anisidine, chloroaniline, bromoaniline, nitroaniline and aminobenzoic acid, pyridines such as dimethylaminopyridine, pyrroles, quinolines and piperidines; metal alkoxides such as sodium methoxide and lithium methoxide; quaternary ammonium hydroxides such as tetramethyl ammonium hydroxide and trimethyl-n-propyl ammonium hydroxide; sulfates, nitrates or chlorides such as ammonium ethyl sulfate, ammonium trimethyl nitrate and anilinium chloride; inorganic bases such as sodium hydrogencarbonate; Grignard reagents such as magnesium ethyl bromide.

The amount of these additives used is preferably 10 equivalents or lower based on one equivalent of the raw compound. If the additives are used in an amount of more than 10 equivalents, the effect of adding the additives is no longer increased. The method for adding the basic compound is not particularly limited. The basic compound may be previously charged into the reaction system before adding the acrylic compound thereto, or may be charged subsequent to addition of the acrylic compound, but it is usually desirable to drop the basic compound together with the acrylic compound. In this case, it is preferable to prevent abnormal rise of the reaction temperature in order to avoid occurrence of undesirable side reactions. As the solvent, there may be suitably used those solvents exhibiting a high dissolvability to the raw compound and the aimed compound. Examples of the solvent include halogen compounds such as dichloromethane, chloroform and 1,2-dichloroethane; ether compounds such as tetrahydrofuran, diethyl ether and methyl t-butyl ether; and hydrocarbon compounds such as benzene and hexane. The reaction temperature is in the range of −70 to 200° C. and preferably −50 to 80° C. If the reaction temperature is lower than −70° C., the reaction rate tend to be lowered, and if the reaction temperature is higher than 200° C., it may be difficult to control the reaction or undesirable side reactions tend to proceed, resulting in deteriorated yield of the aimed compound.

When the acid compounds such as typically acrylic acid and methacrylic acid are used as the acrylic compound, the production process is preferably conducted while removing water by-produced during the reaction by azeotropy using acid catalysts or by a dehydrating agent. The removal of water by azeotropy may be performed using a Dean-Stark water separator, etc. Examples of the suitable acid catalysts include inorganic acids such as sulfuric acid, and organic acids such as benzenesulfonic acid and p-toluenesulfonic acid. As the dehydrating agent, there may be used conventionally known dehydrating agents. Examples of the suitable dehydrating agents include concentrated sulfuric acid, boron trifluoride etherate, trifluoroacetic anhydride, dicyclohexyl carbodiimide, 2-halobenzothiazolium fluoroborate, 2-halogenated pyridinium salts, triphenyl phosphine/carbon tetrachloride and thionyl chloride/basic compound.

When water produced is removed by azeotropy, the solvent used therein may be selected from those solvents that have a high compatibility with water and a high dissolvability to the aimed compound as well as are inert to the reaction of the present invention. In addition, in order to remove the water by-produced during the reaction, the use of such solvents capable of undergoing azeotropy with water is preferred. Examples of such organic solvents include $C_6$ to $C_{10}$ aliphatic hydrocarbons such as hexane, heptane, octane, nonane and decane; $C_6$ to $C_{10}$ alicyclic hydrocarbons such as cyclohexane, methyl cyclohexane, dimethyl cyclohexane and ethyl cyclohexane; and aromatic hydrocarbons such as benzene, toluene and xylene. Examples of the solvents upon using the dehydrating agents include nitrites such as acetonitrile and benzonitrile; amides such as formamide, acetamide, dimethyl formamide and dimethyl acetamide; halogenated hydrocarbons; nitro compounds; esters such as ethyl acetate; ethers such as diethyl ether, diisopropyl ether and dioxane. These solvents may be used singly or in the form of a mixture of any two or more thereof. The solvent may be used in an amount of 0.1 to 20 parts by weight and preferably 1 to 10 parts by weight based on one part by weight of the raw compound. The reaction temperature used for removal of water by azeotropy in the present invention is an azeotropic temperature of the organic solvent used and water. When the dehydrating agent is used, the reaction temperature is not particularly limited to the azeotropic temperature. If the reaction temperature is lower than 60° C., the reaction rate tends to be considerably lowered. On the other hand, if the reaction temperature is higher than 150° C., the selectivity of the aimed compound tends to be lowered.

When the acrylic esters such as methyl acrylate and methyl methacrylate are used as the acrylic compound, corresponding alcohols (methanol in the case of methoxy group, and ethanol in the case of ethoxy group) as produced are removed out of the reaction system by known methods such as distillation to obtain the aimed compound. Examples of the metals and derivatives thereof include metals such as tin, titanium, germanium, zinc, lead, cobalt, iron, zirconium, manganese, antimony and potassium, and derivatives thereof. As the derivatives of metals, there may be preferably used halogen compounds, oxides, carbonates, metal alkoxides, carboxylates, etc. The reaction temperature is in the range of 0 to 200° C. and preferably 50 to 150° C. If the reaction temperature is lower than 0° C., the reaction rate tends to be lowered. On the other hand, if the reaction temperature is higher than 200° C., undesirable side reactions tend to proceed, resulting in deteriorated yield of the aimed compound. When the corresponding alcohols are removed out of the reaction system by distillation, the reaction may be conducted at a temperature near a boiling point of the corresponding alcohols. In this case, the solvent used in the reaction preferably exhibits a high dissolvability to the raw compound and aimed compound as well as is inert to the reaction. Examples of the solvent include halogen compounds such as dichloromethane, chloroform and 1,2-dichloroethane; ether compounds such as tetrahydrofuran, diethyl ether and methyl t-butyl ether; hydrocarbon compounds such as benzene, toluene, hexane and heptane; and nitrile compounds such as acetonitrile.

Also, the hydroxyl groups of the adamantanedialcohol compounds may be alcoholated with alkali metals such as lithium and sodium, alkyl lithium such as butyl lithium or Grignard reagents such as magnesium ethyl bromide, and then subjected to the esterification reaction. More specifically, after the hydroxyl (OH) groups of the adamantanedialcohol compounds are converted into OX groups wherein X is Li, Na, MgBr, MgCl, etc., the esterification reaction may be performed. When the reaction product obtained by the reaction between the 1,3-adamantanedicarboxylic acid derivative and the organic metal compound is already in the form of such an alcoholate, the reaction product may be directly subjected to esterification reaction without the step for producing the adamantanedialcohols. The reaction time required for the esterification reaction of the present invention is 0.5 to 1000 h and preferably 1 to 100 h. However, the reaction time may vary depending upon the reaction temperature, esterification method, etc., and may be determined according to desired yield, etc. Therefore, the reaction time is not particularly limited to the above-specified range.

Upon the esterification reaction, a polymerization inhibitor may be added to the reaction system. As the polymerization inhibitor, there may be used ordinary polymerization inhibitors without any particular limitations. Examples of the polymerization inhibitor include nitroso compounds such as 2,2,6,6-tetramethyl-4-hydroxypiperidine-1-oxyl, ammonium salts of N-nitrosophenylhydroxylamine, aluminum salts of N-nitrosophenylhydroxylamine, ammonium salts of N-nitroso-N-(1-naphthyl)hydroxylamine, N-nitrosodiphenylamine, N-nitroso-N-methyl aniline, nitrosonaphthol, p-nitrosophenol and N,N'-dimethyl-p-nitrosoaniline; sulfur-containing compounds such as phenothiazine, methylene blue and 2-mercaptobenzoimidazole; amines such as N,N'-diphenyl-p-phenylenediamine, N-phenyl-N'-isopropyl-p-phenylenediamine, 4-hydroxydiphenylamine and aminophenol; quinones such as hydroxyquinoline, hydroquinone, methyl hydroquinone, p-benzoquinone and hydroquinone monomethyl ether; phenols such as methoxyphenol, 2,4-dimethyl-6-t-butyl phenol, catechol, 3-s-butyl catechol and 2,2-methylenebis-(6-t-butyl-4-methyl phenol); imides such as N-hydroxyphthalamide; oximes such as cyclohexane oxime and p-quinone dioxime; and dialkylthiodipropionates. The amount of the polymerization inhibitor added is 0.001 to 10% by weight and preferably 0.01 to 1% by weight based on the weight of the acrylic compound.

Upon completion of the reaction, the resultant reaction solution is washed with water to remove an excess amount of the acrylic compounds as well as the additives such as acids and bases. The washing water may contain appropriate inorganic salts such as sodium chloride and sodium hydrogencarbonate. In addition, the reaction solution is washed with alkali to remove unreacted acrylic compounds therefrom. Examples of the alkali component used for the alkali washing include, but are not particularly limited to, an aqueous sodium hydroxide solution, a potassium hydroxide solution and aqueous ammonia. Further, the reaction solution may be washed with an acid to remove metal impurities therefrom. Examples of the acid used for the acid washing include an aqueous hydrochloric acid solution, an aqueous inorganic acid solution such as an aqueous hydrochloric acid solution, an aqueous sulfuric acid solution and an aqueous phosphoric acid solution as well as an aqueous organic acid solution such as an aqueous oxalic acid solution. Also, upon washing the reaction solution, an organic solvent may be further added thereto according to properties of the compound represented by the general formula (1). The organic solvent added to the reaction solution may be the same as or different from that used in the reaction, and it is usually desirable to use such a solvent having a low polarity which is readily separable from water.

In the present invention, the respective reaction steps may be conducted under ordinary pressure, reduced pressure or applied pressure. Further, the reaction may be performed by ordinary methods such as batch method, semi-batch method and continuous method. The derivatives obtained in the respective steps may be isolated in the individual steps, or directly transferred and used in the subsequent steps without isolation thereof. After completion of the reaction, the reaction product may be readily separated and purified by separation methods such as, for example, filtration, concentration, distillation, extraction, crystallization, recrystallization and column chromatography, or combination thereof.

Specific examples of the thus produced compound represented by the general formula (1) include 2-methacryloyloxy-2-(3-(2-methacryloyloxy-2-propyl)-1-adamantyl)propane, 2-acryloyloxy-2-(3-(2-acryloyloxy-2-propyl)-1-adamantyl)propane, 2-perfluoroacryloyloxy-2-(3-(2-perfluoroacryloyloxy-2-propyl)-1-adamantyl)propane, 2-(α-trifluoro)acryloyloxy-(3-(2-α-trifluoro)acryloyloxy-2-propyl)-1-adamantyl)propane, 2-(meth)acryloyloxy-2-(3-(2-(meth)acryloyloxy-2-propyl)-5-hydroxy-1-adamantyl) propane, 2-(meth)acryloyloxy-2-(3-(2-(meth)acryloyloxy-2-butyl)-1-adamantyl)butane, 2-(meth)acryloyloxy-3-(3-(2-(meth)acryloyloxy-3-pentyl)-1-adamantyl)pentane, 2-(meth)acryloyloxy-2-(3-(2-(meth)acryloyloxy-2-propyl)-5,7-dimethyl-1-adamantyl)propane, 2-(meth)acryloyloxy-2-

(3-(2-hydroxy-2-propyl)-1-adamantyl)propane and 2-hydroxy-2-(3-(2-hydroxy-2-propyl)-1-adamantyl)propane. In particular, among these compounds, as the raw material of the functional resin composition, there may be suitably used 2-methacryloyloxy-2-(3-(2-methacryloyloxy-2-propyl)-1-adamantyl)propane, 2-acryloyloxy-2-(3-(2-acryloyloxy-2-propyl)-1-adamantyl)propane, 2-methacryloyloxy-2-(3-(2-hydroxy-2-propyl)-1-adamantyl)propane and 2-acryloyloxy-2-(3-(2-hydroxy-2-propyl)-1-adamantyl)propane.

The functional resin composition of the present invention may be produced by homopolymerizing or copolymerizing these compounds as repeating units. Upon the polymerization, in general, the repeating unit compounds are dissolved in a solvent, and after adding a catalyst, the resultant solution is polymerized while heating or cooling. The polymerization reaction depends upon kind of polymerization initiator used, polymerization initiating method such as heating and light irradiation, and polymerization conditions such as temperature, pressure, concentration, solvent and additives. The functional resin composition of the present invention may be generally produced by radical polymerization method using a radical generator such as azoisobutyronitrile or ionic polymerization method using a catalyst such as alkyl lithium. Also, these polymerization procedures may be conducted by ordinary methods.

Examples of the raw comonomer of the copolymer which is copolymerized with the compound represented by the general formula (1) include adamantylacrylate derivatives such as 2-methyl-2-adamantyl (meth)acrylate, 2-ethyl-2-adamantyl (meth)acrylate, 2-(meth)acryloyloxy-2-(1-adamantyl)propane, 2-(meth)acryloyloxy-2-(1-adamantyl)butane and 3-(meth)acryloyloxy-3-(1-adamantyl)pentane; hydroxystyrene derivatives such as hydroxystyrene, α-methylstyrene, 4-t-butoxystyrene, 4-t-butoxycarbonyloxystyrene, 4-t-butoxycarbonylmethyloxystyrene and 4-(2-t-butoxycarbonylethyloxy)styrene; as well as t-butyl (meth)acrylate, isobornyl (meth)acrylate, tricyclodecanyl (meth)acrylate, β-(meth)acryloyloxy-γ-butyrolactone, β-(meth)acryloyloxy-β-methyl-γ-butyrolactone, α-(meth)acryloyloxy -γ-butyrolactone, α-(meth) acryloyloxy α-methyl-γ-butyrolactone, α-(meth)acryloyloxy-γ,γ-dimethyl-γ-butyrolactone, 5-(meth)acryloyloxy-3-oxatricyclo[4.2.1.0$^{4,8}$]nonane-2-one (=9-(meth)acryloyloxy 2-oxatricyclo[4.2.1.0$^{4,8}$]nonane-3-one) and 6-(meth)acryloyloxy 3-oxatricyclo[4.3.1.1$^{4,8}$]undecane-2-one. These other repeating units may be present singly or in the combination of any two or more thereof.

The functional resin composition of the present invention exhibits a weight-average molecular weight (hereinafter referred to merely as "Mw") of preferably 1000 to 150000 and more preferably 3000 to 100000 as measured in terms of polystyrene by a gel permeation chromatography (GPC). In addition, the ratio of the Mw to a number-average molecular weight (hereinafter referred to merely as "Mn") of the functional resin composition as measured in terms of polystyrene by a gel permeation chromatography (GPC) (Mw/Mn) is usually in the range of 1 to 10 and preferably 1 to 5. In the present invention, the functional resin compositions may be used singly or in the form of a mixture of any two to more thereof.

The functional resin composition of the present invention contains the above high-molecular weight compound and a photo-acid generator in a solvent. Examples of the resin solvent usually used for the above purpose include straight-chain ketones such as 2-pentanone and 2-hexanone; cyclic ketones such as cyclopentanone and cyclohexanone; propylene glycol monoalkyl acetates such as propylene glycol monomethyl ether acetate and propylene glycol monoethyl ether acetate; ethylene glycol monoalkyl ether acetates such as ethylene glycol monomethyl ether acetate and ethylene glycol monoethyl ether acetate: propylene glycol monoalkyl ethers such as propylene glycol monomethyl ether and propylene glycol monoethyl ether; ethylene glycol onoalkyl ethers such as ethylene glycol monomethyl ether and ethylene glycol monoethyl ether; diethylene glycol alkyl ethers such as diethylene glycol dimethyl ether and diethylene glycol diethyl ether; esters such as ethyl acetate and ethyl lactate; alcohols such as cyclohexanol and 1-octanol; ethylene carbonate; and γ-butyrolactone. These solvents may be used singly or in the form of a mixture of any two or more thereof.

The photo-acid generator may be appropriately selected from those usable as an acid generator for chemically-amplified type resist compositions according to a wavelength of exposure light by taking into consideration, a thickness range of resist coating film to be formed as well as an absorptivity coefficient of the photo-acid generator itself. The photo-acid generators may be used singly or in the combination of any two or more thereof. The amount of the photo-acid generator used is in the range of preferably 0.1 to 20 parts by weight and more preferably 0.5 to 15 parts by weight based on 100 parts by weight of the resin.

Examples of the photo-acid generator usable in a far ultraviolet range include onium salt compounds, sulfone imide compounds, sulfone compounds, sulfonic ester compounds, quinone-diazide compounds and diazomethane compounds. Of these compounds, the onium salt compounds such as sulfonium salts, iodonium salts, phosphonium salts, diazonium salts and pyridinium salts are preferably used together with an ArF excimer layer having a wavelength of 193 nm.

Specific examples of the photo-acid generator suitably used together with an ArF excimer layer having a wavelength of 193 nm include triphenylsulfonium triflate, triphenylsulfonium hexafluoroantimonate, triphenylsulfonium naphthalenesulfonate, (hydroxyphenyl)benzylmethylsulfonium toluenesulfonate, diphenyliodonium triflate, diphenyliodonium pyrenesulfonate, diphenyliodonium dodecylbenzenesulfonate and diphenyliodonium hexafluoroantimonate.

Further, the composition of the present invention may contain an acid diffusion controller having such an effect of controlling diffusion of acid generated from the acid generator upon exposure to light in the resist coating film and preventing occurrence of undesirable chemical reactions in non-exposed portions thereof. As the acid diffusion controller, there may be suitably used nitrogen-containing organic compounds whose basicity remains unchanged even upon exposure to light or heat treatment during formation of resist patterns. Examples of the nitrogen-containing organic compounds include amine compounds, e.g., monoalkylamines such as n-hexylamine, n-heptylamine and n-octylamine, dialkylamines such as di-n-butylamine, trialkylamines such as triethylamine, aromatic amines such as aniline, N,N-dimethylaniline, 2-methylaniline, 3-methylaniline, 4-methylaniline, 4-nitroaniline and diphenylamine, and ethylenediamine; amide compounds such as formamide, N,N-dimethylformamide, N,N-dimethylacetamide and N-methylpyrrolidone; urea compounds such as urea; imidazoles such as imidazole and benzimidazole; and pyridines such as pyridine and 4-methylpyridine, as well as 1,4-diazabicyclo[2.2.2]octane. The amount of the acid diffusion controller blended is usually 15 parts by weight or lower, preferably 0.001 to 10 parts by weight and more preferably 0.005 to 5 parts by weight based on 100 parts by weight of the resin.

Further, the functional resin composition of the present invention may also optionally contain various additives used in the conventional chemically-amplified type resist compositions such as, for example, surfactants, quenchers, sensitizers, halation inhibitors, preservatives and stabilizers, and defoamers according to requirements. Examples of the preferred sensitizers blended in the composition include carbazoles, benzophenones, rose bengals and anthracenes.

Examples of the surfactants usable in the present invention include nonionic surfactants such as polyoxyethylene lauryl ether and polyethylene glycol dilaurate, as well as commercially available products marketed under the tradenames "MEGAFAX F173" available from Dainippon Ink & Chemicals, Inc., "L-70001" available from Shin-Etsu Chemical Co., Ltd., "EFTOP EF301", "EFTOP EF303" and "EFTOP EF352" all available from Tochem Products, Co., Ltd., "FLORADE FC430" and "FLORADE FC431" both available from Sumitomo 3M Ltd., "ASAHI GUARD AG710", "SURFLON S-382", "SURFLON SC101", "SURFLON SC102", "SURFLON SC103", "SURFLON SC104", "SURFLON SC105" and "SURFLON SC106" all available from Asahi Glass Co., Ltd., "KP341" available from Shin-Etsu Chemical Co., Ltd., and "POLYFLOW No. 75" and "POLYFLOW No. 95" both available from Kyoeisha Chemical Co., Ltd.

The functional resin composition of the present invention is formed into resist patterns by applying the above-prepared solution of the composition on a substrate made of, for example, silicon wafer, metal, plastic material, glass or ceramic material by an appropriate coating means such as a spin coater, a dip coater and a roll coater to form a resist coating film thereon, followed by heat-treating the resist coating film at a temperature of about 50 to 200° C., if required; and then exposing the resist coating film to light through a predetermined mask. The resist coating film has a thickness of, for example, 0.1 to 20 μm and preferably about 0.3 to 2 μm. The exposure procedure may be conducted using rays having various wavelengths, for example, ultraviolet rays and X-rays. The light source may be appropriately selected from far ultraviolet rays such as $F_2$ excimer laser (wavelength: 157 nm), ArF excimer layer (wavelength: 193 nm) and KrF excimer laser (wavelength: 248 nm), extreme ultraviolet rays (wavelength: 13 nm), X-rays, electron beams, etc. Also, the exposure conditions such as exposure amount may also be appropriately determined according to formulation of the functional resin composition and kinds of respective additives.

In the present invention, in order to stably form fine resist patterns with a high accuracy, the resist film after exposure to light is preferably heat-treated at a temperature of 50 to 200° C. for 30 s or more. In this case, when the heat-treating temperature is lower than 50° C., the sensitivity of the resist film tends to be fluctuated over a broad range according to the kind of substrate used. Thereafter, the exposed resist film is developed with an alkali developer usually at a temperature of 10 to 50° C. for a period of 10 to 200 s and preferably at a temperature of 20 to 25° C. for a period of 15 to 90 s, thereby forming predetermined resist patterns.

As the alkali developer, there may be used, for example, an aqueous alkali solution prepared by dissolving an alkali compound such as alkali metal hydroxides, aqueous ammonia, alkylamines, alkanolamines, heterocyclic amines, tetraalkylammoniumhydroxides, choline, 1,8-diazabicyclo-[5.4.0]-7-undecene and 1,5-diazabicyclo-[4.3.0]-5-nonene in water such that a concentration of the alkali is usually 1 to 10% by weight and preferably 1 to 3% by weight. In addition, the alkali developer may further contain an appropriate amount of a water-soluble organic solvent or surfactant.

EXAMPLES

The present invention is described in more detail below with reference to the following examples. However, it should be noted that the following examples are only illustrative and not intended to limit the invention thereto.

Example 1

The synthesis of 2-methacryloyloxy-2-(3-(2-hydroxy-2-propyl)1-1-adamantyl)propane was performed by the following method. First, according to the method described in Japanese Patent Application Laid-open No. 2002-167342, 1000 g of 1,3-dihydroxyadamantane was synthesized from adamantane. Next, a four-necked flask equipped with a stirrer, a thermometer, a dropping funnel and a Dimroth condenser was charged with 100 g of 1,3-dihydroxyadamantane, 500 mL of 1,2-dichloroethane and 800 g of 96% sulfuric acid, and further 300 g of formic acid was dropped into the flask for 1 h. Thereafter, the contents of the flask were reacted at 25° C. for 10 h. The resultant reaction solution was filtered to separate precipitated crystals therefrom. The thus separated crystals were washed with water to obtain 140 g of 1,3-adamantanedicarboxylic acid. Then, a four-necked flask equipped with a stirrer, a thermometer and a Dimroth condenser was charged with 140 g of 1,3-adamantanedicarboxylic acid, 12 g of 96% sulfuric acid, 200 g of methanol and 1000 mL of 1,2-dichloroethane, and the contents of the flask were reacted at 62° C. for 10 h.

After completion of the reaction, the resultant reaction solution was separated into an organic phase and a water phase. The organic phase was washed with a saturated sodium hydrogencarbonate aqueous solution, and then concentrated. The thus obtained crystals were separated from the organic phase by filtration, thereby obtaining 150 g of methyl 1,3-adamantanedicarboxylate. Next, a four-necked flask equipped with a stirrer, a thermometer, a Dimroth condenser and a dropping funnel was charged with 100 g of methyl 1,3-adamantanedicarboxylate and 500 mL of tetrahydrofuran, and then 600 mL of a 3M magnesium methyl bromide/diethyl ether solution was dropped into the flask for 1 h. Thereafter, the contents of the flask were stirred at 25° C. for 3 h, and then mixed with water to terminate the reaction. The resultant reaction solution was separated into an organic phase and a water phase. The thus separated organic phase was concentrated to obtain 90 g of 1,3-adamantanediisopropanol.

Figure 1:
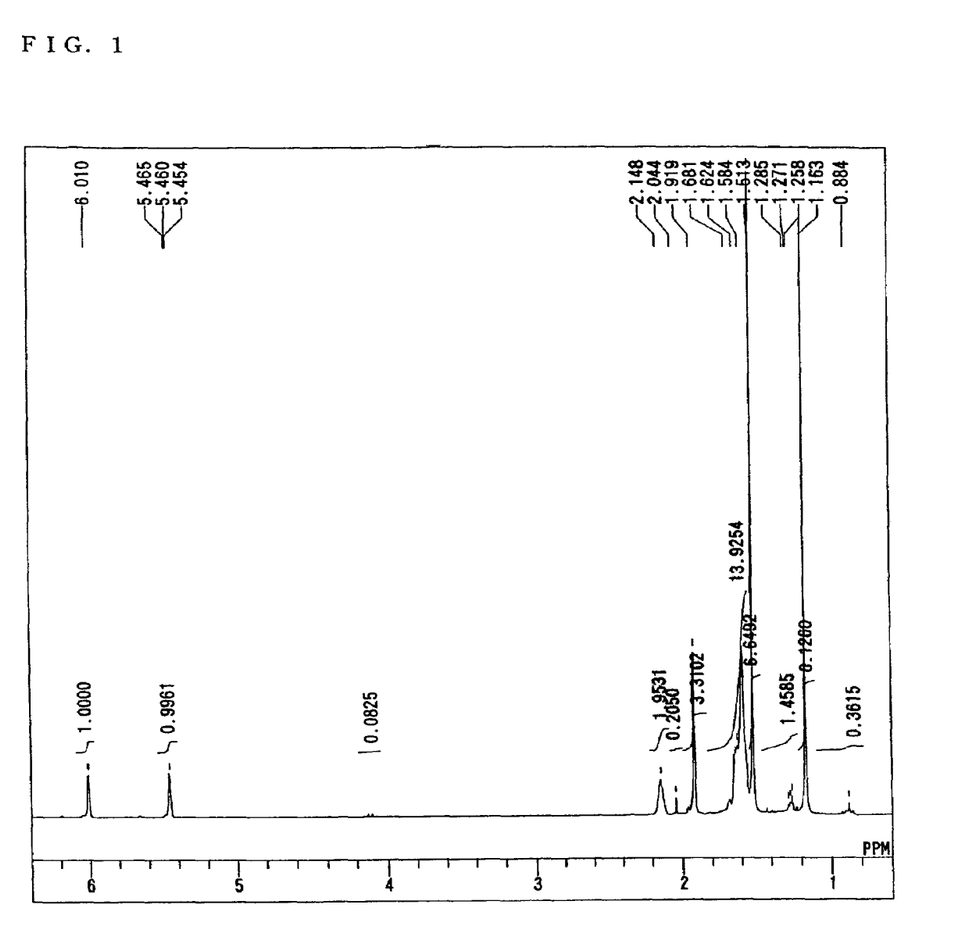
FIG. 1 is a view showing $^1$H-NMR spectrum (270 MHz; $CDCl_3$) of the compound A obtained in Example 1.
Figure 2:
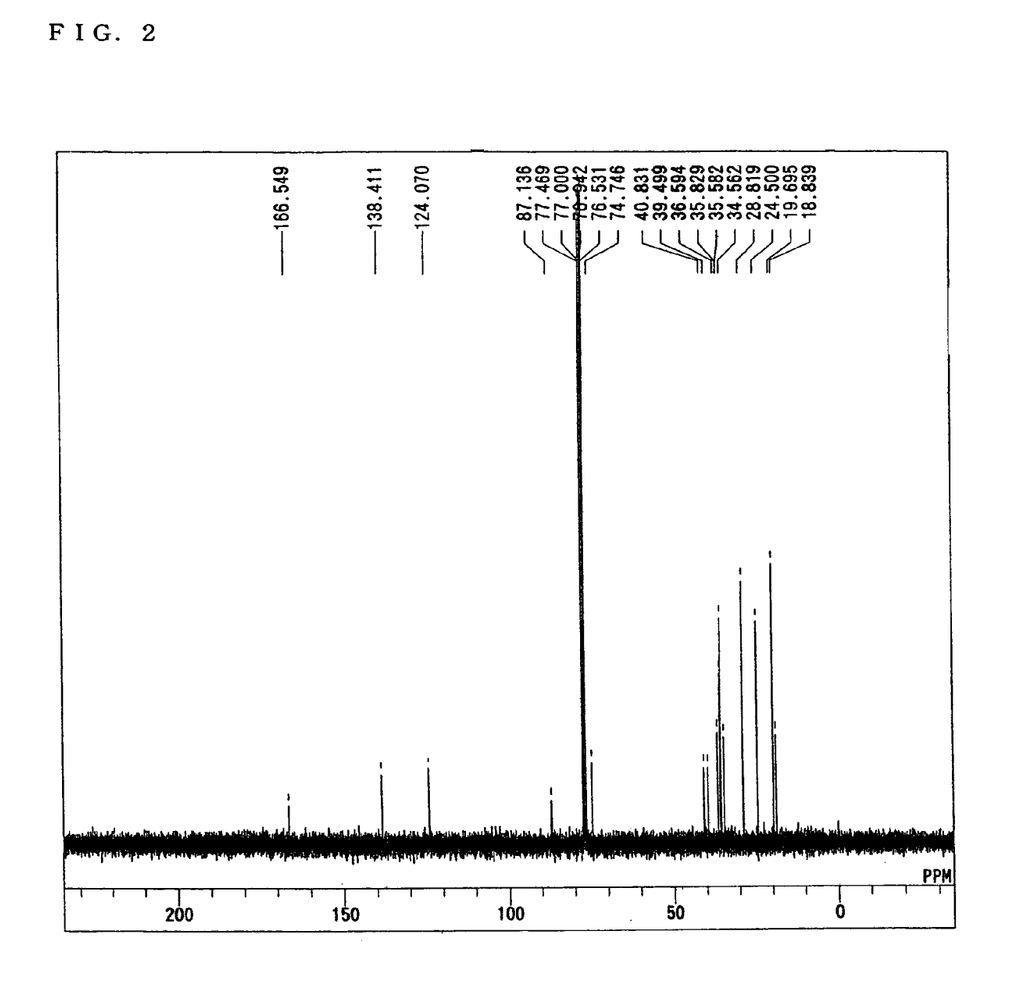
FIG. 2 is a view showing $^{13}$C-NMR spectrum (270 MHz; $CDCl_3$) of the compound A obtained in Example 1.

Next, a five-necked flask equipped with a stirrer, a thermometer, a Dimroth condenser and two dropping funnels was charged with 90 g of 1,3-adamantanediisopropanol and 100 mL of 1,2-dichloroethane, and then 63 g of methacryloyl chloride and 81 g of triethylamine were simultaneously dropped into the flask for 1 h. Thereafter, the contents of the flask were stirred at 25° C. for 3 h, and then mixed with water to terminate the reaction. The resultant reaction solution was separated into an organic phase and a water phase. The thus separated organic phase was washed with ion-exchanged water, filtered, concentrated and then purified by silica gel column chromatography to obtain 80 g of 2-methacryloyloxy-2-(3-(2-hydroxy-2-propyl)-1-adamantyl)propane as represented by the following formula (hereinafter referred to as "compound A"). The thus obtained compound A was identified by $^1$H-NMR and $^{13}$C-NMR (refer to FIGS. 1 and 2).

Synthesis Example 1

Sixty grams of 2-methacryloyloxy-2-(3-(2-hydroxy-2-propyl)-1-adamantyl)propane, 70 g of 2-methyl-2-adamantyl methacrylate, 30 g of methacryloyloxy-γ-butyrolactone and 6 g of azobisisobutyronitrile were dissolved in 160 g of methyl isobutyl ketone, and polymerized in a nitrogen atmosphere at 70° C. for 16 h. After completion of the polymerization, the obtained reaction solution was dropped in a large amount of n-hexane to solidify and purify a resin produced. The resultant white powder was separated by filtration and dried under reduced pressure at 50° C. over one night. The obtained resin had Mw of 11500 and Mw/Mn of 1.6. In addition, as a result of $^{13}$C-NMR analysis, it was confirmed that the molar ratio of 2-methacryloyloxy-2-(3-(2-hydroxy-2-propyl)-1-adamantyl)propane:2-methyl-2-adamantyl methacrylate:methacryloyloxy-γ-butyrolactone in the obtained copolymer resin was 30:50:20. The thus obtained resin was regarded as resin A.

Synthesis Example 2

Fifty grams of 2-methacryloyloxy-2-(3-(2-hydroxy-2-propyl)-1-adamantyl)propane, 30 g of methacryloyloxy-γ-butyrolactone and 3 g of azobisisobutyronitrile were dissolved in 80 g of methyl isobutyl ketone, and polymerized in a nitrogen atmosphere at 70° C. for 16 h. After completion of the polymerization, the obtained reaction solution was dropped in a large amount of n-hexane to solidify and purify a resin produced. The resultant white powder was separated by filtration and dried under reduced pressure at 50° C. over one night. The obtained resin had Mw of 12300 and Mw/Mn of 1.5. In addition, as a result of $^{13}$C-NMR analysis, it was confirmed that the molar ratio of 2-methacryloyloxy-2-(3-(2-hydroxy-2-propyl)-1-adamantyl)propane: methacryloyloxy-γ-butyrolactone in the obtained copolymer resin was 60:40. The thus obtained resin was regarded as resin B.

Synthesis Example 3

Fifty grams of 2-methyl-2-adamantyl methacrylate, 50 g of 3-hydroxy-1-adamantyl methacrylate, 40 g of methacryloyloxy-γ-butyrolactone and 6 g of azobisisobutyronitrile were dissolved in 160 g of methyl isobutyl ketone, and polymerized in a nitrogen atmosphere at 70° C. for 16 h. After completion of the polymerization, the obtained reaction solution was dropped in a large amount of n-hexane to solidify and purify a resin produced. The resultant white powder was separated by filtration and dried under reduced pressure at 50° C. over one night. The obtained resin had Mw of 11000 and Mw/Mn of 1.6. In addition, as a result of $^{13}$C-NMR analysis, it was confirmed that the molar ratio of 2-methyl-2-adamantyl methacrylate:3-hydroxy-1-adamantyl methacrylate: methacryloyloxy-γ-butyrolactone in the obtained resin was 40:35:25. The thus obtained resin was regarded as resin C.

Example 2

One hundred parts by weight of the resin A produced in SYNTHESIS EXAMPLE 1 and 10 parts by weight of triphenylsulfonium hexafluoroantimonate were mixed with ethyl lactate as a solvent to prepare a photoresist resin composition having a resin concentration of 15% by weight. The thus obtained photoresist resin composition was applied onto a silicon wafer by a spin-coating method to form a photosensitive layer having a thickness of 0.5 μm thereon. The obtained photosensitive layer was pre-baked on a hot plate at 100° C. for 150 s, successively exposed to light using an ArF excimer laser with a wavelength of 193 nm at an exposure rate of 20 mJ/cm² through a mask, and then post-baked at 100° C. for 60 s. Next, the exposed layer was developed with a 0.3M tetramethyl ammonium hydroxide aqueous solution for 60 s, and then rinsed with pure water to obtain 0.20 μm-pitch line-and-space patterns.

Example 3

The same procedure as in EXAMPLE 2 was repeated except for using the resin B obtained in SYNTHESIS EXAMPLE 2 instead of the resin A. The thus obtained patterns were evaluated.

Comparative Example 1

The same procedure as in EXAMPLE 2 was repeated except for using the resin C obtained in SYNTHESIS EXAMPLE 3 instead of the resin A. The thus obtained patterns were evaluated.

The respective resist patterns thus formed from the above resins A, B and C were examined to measure the difference between the broadest and narrowest line widths (line edge roughness) using SEM. As a result, it was confirmed that the resist patterns formed from the resin A containing 2-methacryloyloxy-2-(3-(2-hydroxy-2-propyl)-1-adamantyl)propane were fine patterns with a low line edge roughness and a high accuracy, and the resist patterns formed from the resin B that contained 2-methacryloyloxy-2-(3-(2-hydroxy-2-propyl)-1-adamantyl)propane but was reduced in number of components added thereto also showed good results. In addition, the resist coating film obtained after pre-baking was subjected to measurement of its etching velocity by $CF_4$ gas using a reactive etching apparatus, so that it was confirmed that the etching velocity was high. Further, as a result of observation by SEM, it was confirmed that the resist patterns were free from defects such as separation or peeling, and, therefore, showed an excellent adhesion to substrate. Accordingly, it was recognized that the resist patterns formed from the resins A and B were excellent in all of line edge width, etching velocity and adhesion to substrate as compared to the resist patterns formed from the existing resin C.

TABLE 1

|  | Example 2 (resin A) | Example 3 (resin B) | Comparative Example 1 (resin C) |
| --- | --- | --- | --- |
| Etching velocity | 0.95 | 0.93 | 1.00 |
| Line edge roughness | 6.8 nm | 8.3 nm | 10.7 nm |
| Adhesion to substrate* | X | Y | Z |

Note
*The adhesion to substrate was evaluated by observing separation or peeling of resist patterns by SEM and classifying the results into ranks X (excellent), Y (good) and Z (poor).

Example 4

The synthesis of 2-methacryloyloxy-2-(3-(2-methacryloyloxy-2-propyl)-1-adamantyl)propane was performed by the following method. First, according to the method described in Japanese Patent Application Laid-open No. 2002-167342, 100 g of 1,3-dihydroxyadamantane was synthesized from adamantane. Next, a four-necked flask equipped with a stirrer, a thermometer, a dropping funnel and a Dimroth condenser was charged with 100 g of 1,3-dihydroxyadamantane, 500 mL of 1,2-dichloroethane and 800 g of 96% sulfuric acid, and further 300 g of formic acid was dropped into the flask for 1 h. Thereafter, the contents of the flask were reacted at 25° C. for 10 h. The resultant reaction solution was filtered to separate precipitated crystals therefrom. The thus separated crystals were washed with water to obtain 140 g of 1,3-adamantanedicarboxylic acid.

Then, a four-necked flask equipped with a stirrer, a thermometer and a Dimroth condenser was charged with 140 g of 1,3-adamantanedicarboxylic acid, 12 g of 96% sulfuric acid, 200 g of methanol and 1000 mL of 1,2-dichloroethane, and the contents of the flask were reacted at 62° C. for 10 h. After completion of the reaction, the resultant reaction solution was separated into an organic phase and a water phase. The thus separated organic phase was washed with a saturated sodium hydrogencarbonate aqueous solution, and then concentrated. The obtained crystals were separated by filtration from the organic phase, thereby obtaining 150 g of methyl 1,3-adamantanedicarboxylate. Next, a four-necked flask equipped with a stirrer, a thermometer, a Dimroth condenser and a dropping funnel was charged with 100 g of methyl 1,3-adamantanedicarboxylate and 500 mL of tetrahydrofuran, and then 600 mL of a 3M magnesium methyl bromide/diethyl ether solution was dropped into the flask for 1 h. Thereafter, the contents of the flask were stirred at 25° C. for 3 h, and then mixed with water to terminate the reaction. The resultant reaction solution was separated into an organic phase and a water phase. The thus separated organic phase was concentrated to obtain 90 g of 1,3-adamantanediisopropanol which was identified by $^1$H-NMR and $^{13}$C-NMR.

Figure 3:
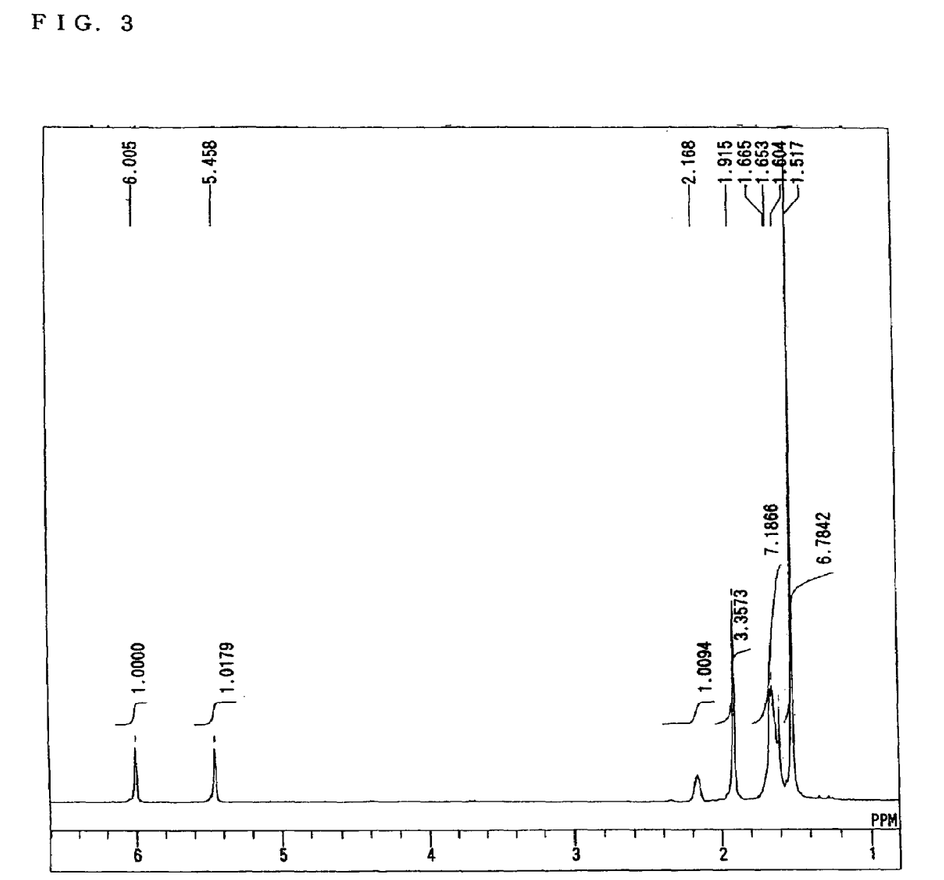
FIG. 3 is a view showing $^1$H-NMR spectrum (270 MHz; $CDCl_3$) of the compound B obtained in Example 4.
Figure 4:
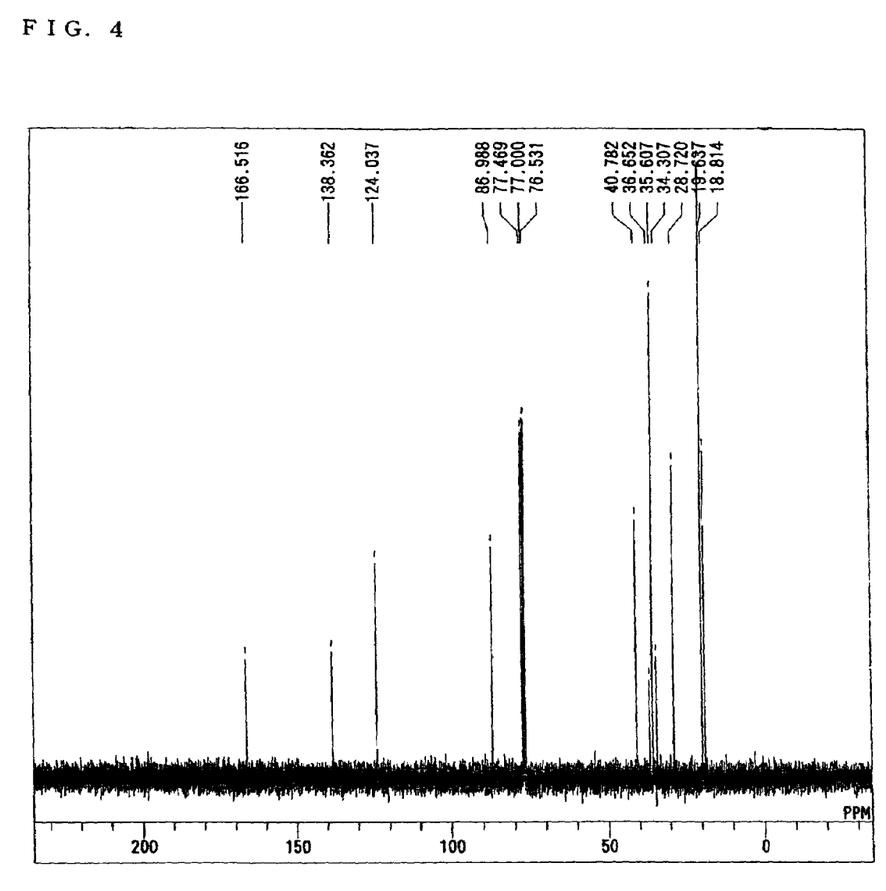
FIG. 4 is a view showing $^{13}$C-NMR spectrum (270 MHz; $CDCl_3$) of the compound B obtained in Example 4.

Next, a five-necked flask equipped with a stirrer, a thermometer, a Dimroth condenser and two dropping funnels was charged with 90 g of 1,3-adamantanediisopropanol and 100 mL of 1,2-dichloroethane, and then 126 g of methacryloyl chloride and 162 g of triethylamine were simultaneously dropped into the flask for 1 h. Thereafter, the contents of the flask were stirred at 25° C. for 3 h, and then mixed with water to terminate the reaction. The resultant reaction solution was separated into an organic phase and a water phase. The thus separated organic phase was washed with ion-exchanged water, filtered, concentrated and then purified by silica gel column chromatography to obtain 80 g of 2-methacryloyloxy-2-(3-(2-methacryloyloxy-2-propyl)-1-adamantyl)propane as represented by the following formula (hereinafter referred to as "compound B"), and the compound B was identified by $^1$H-NMR and $^{13}$C-NMR (refer to FIGS. 3 and 4).

Also, 10 g of 2-methacryloyloxy-2-(3-(2-hydroxy-2-propyl)-1-adamantyl)propane was obtained (which was identified by $^1$H-NMR and $^{13}$C-NMR).

Next, the effect of adding the compound B was examined as follows. As a base resin, there was used a terpolymer resin produced from 2-methyl-2-adamantyl methacrylate, 3-hydroxy-1-adamantyl methacrylate and methacryloyloxy-γ-butyrolactone. More specifically, 50 g of 2-methyl-2-adamantyl methacrylate, 50 g of 3-hydroxy-1-adamantyl methacrylate, 40 g of methacryloyloxy-γ-butyrolactone and 6 g of azobisisobutyronitrile were dissolved in 160 g of methyl isobutyl ketone, and further 1 g of the compound B was added to the obtained solution. The obtained mixture was polymerized in a nitrogen atmosphere at 70° C. for 16 h. After completion of the polymerization, the obtained reaction solution was dropped into a large amount of n-hexane to solidify and purify a resin produced. The resultant white powder was separated by filtration and dried under reduced pressure at 50° C. over one night, thereby obtaining a resin containing the compound B copolymerized. For comparative purpose, a resin containing no compound B was produced.

One hundred parts by weight of each of the thus obtained two kinds of resins and 10 parts by weight of triphenylsulfonium hexafluoroantimonate were mixed with ethyl lactate as a solvent to prepare a photoresist resin composition having a resin concentration of 15% by weight. The thus obtained photoresist resin composition was applied onto a silicon wafer by a spin-coating method to form a photosensitive layer having a thickness of 0.5 μm thereon. The obtained photosensitive layer was pre-baked on a hot plate at 100° C. for 150 s, successively exposed to light using an ArF excimer laser with a wavelength of 193 nm at an exposure rate of 20 mJ/cm$^2$ through a mask, and then post-baked at 100° C. for 60 s. Next, the exposed layer was developed with a 0.3M tetramethylammoniumhydroxide aqueous solution for 60 s, and then rinsed with pure water to obtain 0.20 μm-pitch line-and-space patterns. As a result, it was confirmed that the resin containing the compound B enabled formation of high-contrast patterns as compared to the resin containing no compound B.

INDUSTRIAL APPLICABILITY

The adamantane derivatives of the present invention are useful as crosslinking-type resins, optical materials such as optical fibers, light wave guides, optical disk substrates and photoresists as well as raw materials thereof, intermediate products of medicines and agricultural chemicals, and various other industrial products. Also, the functional resin compositions of the present invention can be used as raw resist materials for KrF, ArF or $F_2$ excimer laser, or chemically amplified type resists for X-rays, electron beams or EUV (extreme ultraviolet rays).

What is claimed is:

1. A compound represented by the general formula (1):

(1)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and one of $Y_1$ and $Y_2$ is a group represented by the general formula (2):

(2)

wherein $R_5$ to $R_7$ may be the same or different from each other and are independently a hydrogen atom, alkyl, halogen or halogen-containing alkyl, and the other one of $Y_1$ and $Y_2$ is a hydrogen atom.

2. The compound according to claim 1, wherein $Y_1$ is a group represented by said general formula (2).

3. The compound according to claim 1, wherein $Y_2$ is a group represented by said general formula (2).

4. A compound represented by the general formula (1):

(1)

wherein X is a hydrogen atom, alkyl, halogen-containing alkyl, halogen, or hydroxyl-, halogen-, nitrile- or ether-containing hydrocarbyl, and a plurality of X groups, if any, may be the same or different from each other; $n_1$ is an integer of 1 to 14; $R_1$ to $R_4$ may be the same or different from each other and are independently alkyl or halogen-containing alkyl; and $Y_1$ and $Y_2$ are each a group represented by the general formula (2):

(2)

wherein $R_5$ to $R_7$ may be the same or different from each other and are independently a hydrogen atom, alkyl, halogen or halogen-containing alkyl.

* * * * *